United States Patent [19]

Tsuji et al.

[11] 4,408,880
[45] Oct. 11, 1983

[54] LASER NEPHELOMETRIC SYSTEM

[75] Inventors: Yashuhiro Tsuji, Kawaguchi; Kiyoshige Wakabayashi, Ohmiya; Mitsuo Watanabe, Machida, all of Japan

[73] Assignee: Chugai Seiyaku Kabushiki Kaisha, Tokyo, Japan

[21] Appl. No.: 304,578

[22] Filed: Sep. 22, 1981

[51] Int. Cl.³ ............................................... G01N 21/00
[52] U.S. Cl. ..................................... 356/338; 250/574; 364/525
[58] Field of Search ............... 356/338, 339; 250/574; 364/525, 555, 524, 575

[56] References Cited

U.S. PATENT DOCUMENTS

| | | |
|---|---|---|
| 3,807,630 | 4/1974 | Stewart . |
| 3,967,901 | 7/1976 | Rodriguez . |
| 4,015,135 | 3/1977 | Tipton, Jr. ........................ 250/574 |
| 4,110,044 | 8/1978 | Pettersson et al. ............. 250/574 X |
| 4,140,395 | 2/1979 | Kreikebaum .................. 250/574 X |

Primary Examiner—John K. Corbin
Assistant Examiner—Matthew W. Koren
Attorney, Agent, or Firm—Fleit, Jacobson & Cohn

[57] ABSTRACT

A laser nephelometric system measures the concentration of various substances in a solution particularly in blood or serum. The system receives a number of data elements each indicative of the intensity of light scattered from the solution at its sampling time. These data elements are processed in accordance with a statistical analysis. Based upon the fact that the relative variation of the scattered light intensity increases as the scattered light decreases, a first screening of data elements is performed so that the band of selection for data elements accords with the above fact. Further a second screening of data elements is performed in order to reduce the effect of the unnecessary light resulting from the other reflecting objects, such as dust, air bubbles and other substances. The average of the screened data elements provides an accurate value of the intensity of scattered light due to the substances to be measured, i.e. measurand.

5 Claims, 2 Drawing Figures

LASER NEPHELOMETRIC SYSTEM

FIELD OF THE INVENTION

This invention relates to a laser nephelometric system for measuring the concentration of various substances or particles in a solution based on scattering of part of the incident laser light, and particularly to a data processing apparatus for processing such scattered light data.

This invention is capable of providing more accurate and higher reliable quantitative analysis of the concentration of substances by processing the scattered light data through a statistical analysis.

BACKGROUND OF THE INVENTION

When a laser nephelometer measures the concentration of plasma protein and pharmacon in a tested solution, the dust, air bubbles and other substances (e.g. lipoprotein, denatured protein) inherently present in that solution usually become the main error causing elements. Accordingly, if the effect of these elements on the scattered data should be eliminated, this would result in a more accurate and reliable measurement.

The Japanese patent public disclosure No. 90883/1976 describes an apparatus for measuring the concentration of light reflecting substances in a solution. Out of the sampled data elements, only the element representing the scattered light having the least intensity is accepted while any other data element is rejected. The apparatus uses this minimum data element as a "measured value". Further, this patent public disclosure contemplates a method of reducing the effect of dust particles and air bubbles by differentiating a momentary pulsed output resulting from the scattering caused by those particles and bubbles from the uniform output resulting from the substances which are the object of measurement.

The method as disclosed in the Japanese Patent Public Disclosure No. 120485/1978 stores all observed data elements and changes their order in accordance with the data value indicative of the scattered light intensity at the time of sampling so that the data element having the minimum value is placed in the first position. A predetermined number of data elements including and following the minimum data element are all added together and averaged. The average value is indicated by indicating means in the form of digital representation or print out.

However, dust particles and air bubbles present in suspension in the small space where the laser beam travels cannot be taken out from that space. Accordingly, the above average with respect to the predetermined number of data elements including and following the minimum data element may still have, to a certain extent, error factors due to those dust particles and air bubbles.

SUMMARY OF THE INVENTION

It is therefore the main object of this invention to provide a more accurate and reliable laser nephelometric system.

Another object of this invention is to provide the above mentioned nephelometric system which processes a number of scattered light data elements through statistical analysis in accordance with the scattering characteristics of the solution containing the substances to be measured.

In accordance with this invention, a plurality of sampled data elements each indicative of the scattered light intensity as detected at the time of sampling are stored. The data element having the minimum data value is searched out from these data elements. This minimum data element is used as a lower limit for selection or screening of data elements. An upper limit is determined from the value of the minimum data element. The lower and upper limits define a range for acceptance or screening of data elements. That is, only those data elements that have values within the range are accepted or selected while the other elements are rejected. An average value is obtained by averaging the accepted data elements. Using this average value as a reference, a second range is determined, extending from a second lower to a second upper limit said limits being smaller and greater than the average value, respectively. The second range is used for second screening of data elements. That is, only those data elements that have values within the second range are selected and averaged to produce a second average value. Based upon the fact that the relative variation in scattered light intensity becomes greater as the light intensity decreases, this invention sets the relative width of the above first range to be a function of the minimum value of scattered light data so that it becomes more extensive as the minimum value decreases. Further, the above second range is set to be a function of the standard deviation of the first selected data elements. Thus, accuracy of measurement is improved.

DETAILED DESCRIPTION OF THE PREFERRED EMBODIMENT

Figure 1:
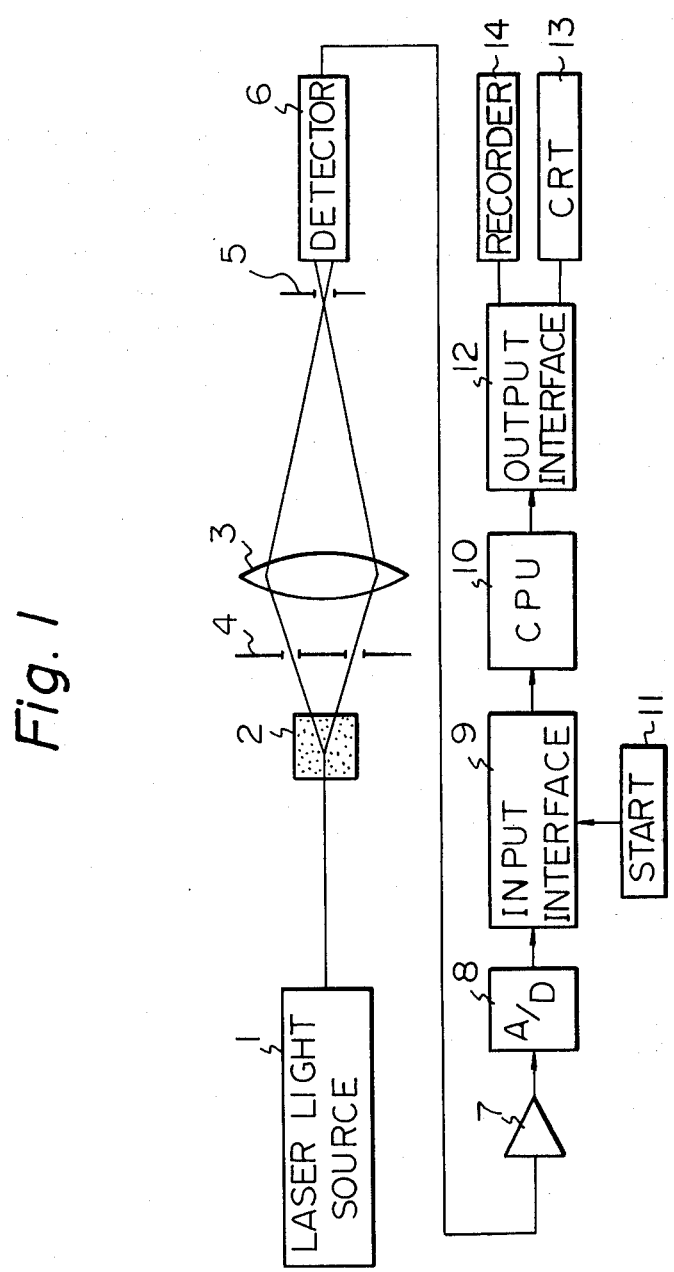
FIG. 1 is a diagram illustrating the laser nephelometric system in accordance with this invention.

FIG. 1 is a diagram illustrating the laser nephelometric system in accordance with this invention. Reference numeral 1 designates a source of laser light. A sampled cuvette 2 is placed in the axis of the laser light path. A lens assembly 3 concentrates the light that has been scattered in the cuvette 2 and has passed through a slit board 4 for allowing a limited field of vision. Reference numeral 5 designates another slit board which is appropriately placed in the path of light from the lens assembly 3. A light detector 6 is placed behind the slit board 5 to detect the scattered light.

Accordingly, when a laser beam is emitted from the source 1, it enters into the tested cuvette in which the light is scattered. Part of the scattered light which is within the field of vision limited by the slit board can pass through the slits and is concentrated by the lens 3. Then, the light passes through the slit board 5 and falls upon the light detector 6 in which the light is converted into an electric signal.

Reference numeral 7 is an amplifier which is connected to the output of the light detector 6 to amplify the electric signal to pass it to an analogue-to-digital convertor 8. Reference numeral 9 designates an input interface the output of which is connected to a central processing unit (CPU) for performing the processing of the sampled data in response to a start signal from a starting circuit 11. The data processed in CPU is output through an output interface 12 and may be recorded and displayed by a recording device 14 and cathode ray tube 13.

Figure 2:
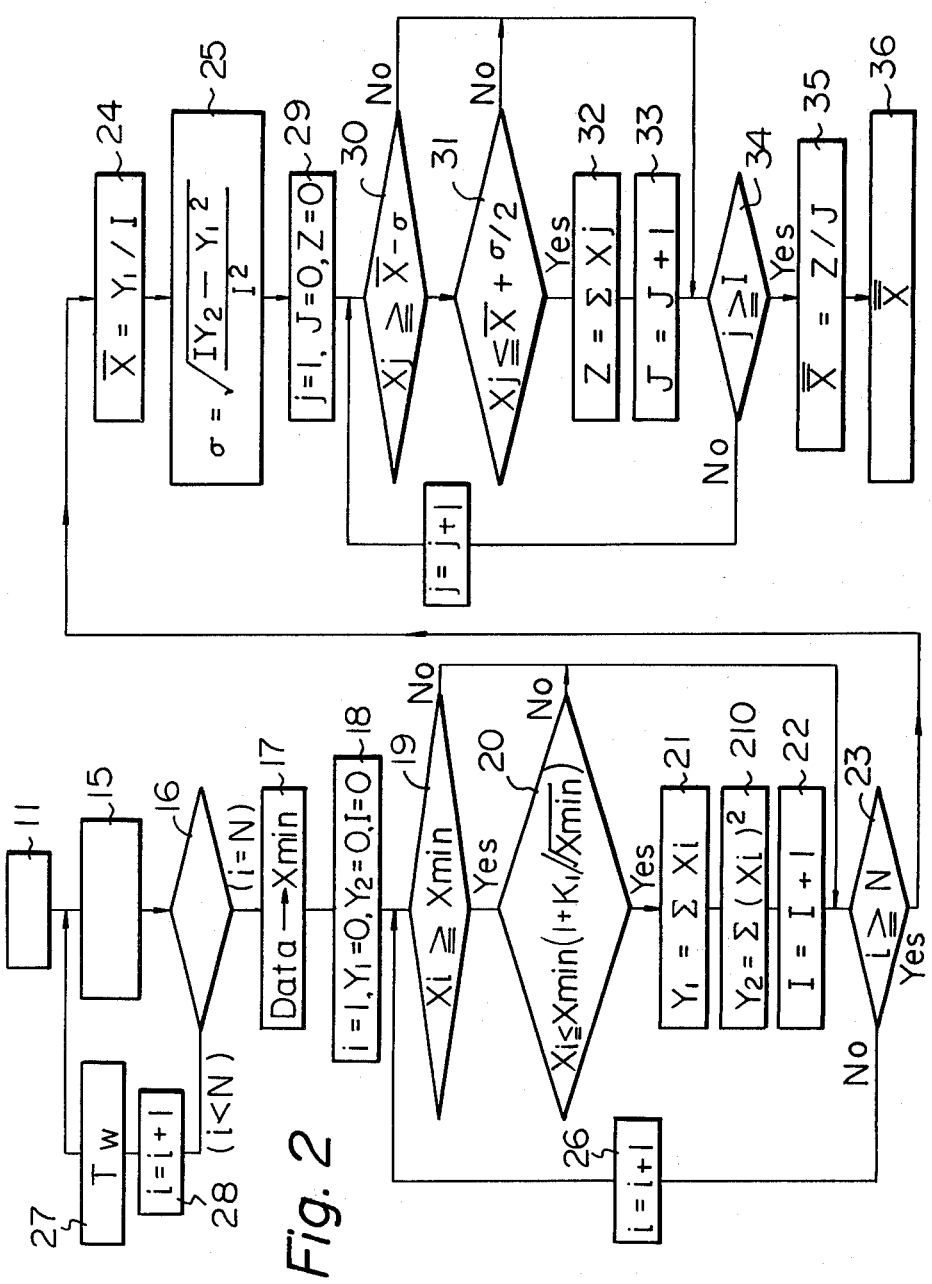
FIG. 2 is a flow chart of data processing performed by the central processing unit in FIG. 1.

FIG. 2 is a flow chart of data processing performed by the central processing unit. Reference numeral 15 designates a data storing function for receiving a predetermined number N of the sampled data elements Xi (i=1, 2, ... N). A decision box 16 decides whether the data storing is finished.

If i is less than N, this means that the data storage is not completed. An incrementing function 28 increments the number i of the data element to "i+1". After a predetermined delay Tw given by a delay function 27, the next data element is received.

After receiving the predetermined number N of data elements, the computer advances toward a minimum value data element searching function 17. This function detects the minimum data value Xmin among the number N of received data elements each indicative of the scattered light intensity.

Reference numeral 18 designates an initializing function in the data processing which sets the number i of data element, the sum $Y_1$ of the selected data elements, the sum $Y_2$ of the square of the selected data elements, and the number N of selected data elements to "1", "0", "0", and "0", respectively.

Next, out of the number N of the data elements, only those data elements that are within a certain range A from the minimum value Xmin are selected. An example of this certain range A is a range extending from Xmin to Xmin $(1+K_1\sqrt{Xmin})$ (where $K_1$ is constant) which will be described in this embodiment. Reference numeral 19 is a lower limit deciding function for deciding whether the data elements Xi is greater than Xmin. Reference numeral 20 is a data upper limit deciding function for deciding whether the data element Xi is smaller than Xmin $(1+K_1/\sqrt{Xmin})$.

Reference numeral 21 designates a function for summing up data elements. Reference numeral 210 designates a function for summing up the squared data elements. Reference numeral 22 is a function for counting up the number of the selected data elements.

Accordingly, only when a data element satisfies the conditions given by the data lower limit function 19 and the data upper limit function 20, is that data element added to the sum $Y_1$ in the data element summing function 21 and to the sum $Y_2$ in the squared data element summing function 210 and then the number I of selected data elements in the function 22 is increased by one.

If a data element does not satisfy the above conditions, that data element is rejected without changing the sums $Y_1$ and $Y_2$.

The upper limit for selection or acceptance of data elements is expressed as follows:

$$Xmin\ (1 + K_1/\sqrt{Xmin}\ ) = Xmin + K_1 \sqrt{Xmin}\ .$$

This utilizes the fact that the relative variation of the light intensity becomes greater as Xmin decreases. Accordingly, it is advantageous to extend the range of acceptance for smaller Xmin. This is confirmed by dividing the above conditions by Xmin to obtain $$1 \leq \frac{Xi}{Xmin} \leq 1 + \frac{K_1}{\sqrt{Xmin}}$$

This formula teaches that a more extensive range is given as Xmin decreases.

The formula for the upper limit may be generalized as follows:

Upper limit = Xmin [1+f(Xmin)] wherein f(Xmin) is a function of the value of minimum data element Xmin which decreases as Xmin increases. The function f(Xmin) determines the relative width of the selection range.

Reference numeral 23 is a function for deciding whether the processing of all data elements is completed. Reference numeral 26 is a function for incrementing, in a similar manner to the data element number incrementing function 28 as previously described, the number of data elements until all data elements are processed.

Accordingly, the arrangement comprising the above initializing function 18, data lower limit deciding function 19, data upper limit deciding function 20, data element summing up function 21, squared data element summing up function 210, selected data number counting up function 22, deciding function 23 for deciding whether the data element selection is completed and data element number incrementing function 26, serves to determine whether each data element Xi is within the range Xmin$\leq$Xi$\leq$Xmin $(1+K_1/\sqrt{Xmin})$, to reject any element without the range, and to accept any element within the range for adding it to the sum of the data elements and to the sum of the squared data elements and counting up the number of accepted data elements. Reference numeral 24 designates a first average calculating function. When the differentiating of acceptance and rejection of the number N of data elements is completed, the function 24 obtains an average value $\overline{X}$ with respect to the number I of the accepted data elements.

Reference numeral 25 is a standard deviation calculating function. By this function, a standard deviation $\sigma$ is obtained as a result of the calculation $$\sigma = \sqrt{\frac{IY_2 - Y_1^2}{I^2}}\ .$$

Next, among the number I of the data elements, only those data elements that are within a certain range B including $\overline{X}$ are accepted. An example of the range B is a range extending from $(\overline{X}-\sigma)$ to $(\overline{X}+\sigma/2)$ which will be described in this embodiment.

Data elements are renumbered with respect to the number I of the accepted data elements. The new number is expressed by suffix j. Since the number of the accepted data elements within the range A is I, it follows $1\leq j \leq I$.

Reference numeral 29 is an initializing function which sets data number j to "1" and sets the sum Z of accepted (finally accepted) data elements and the number J of accepted (finally accepted) data element to "0" (zeros).

Reference numeral 30 designates a data lower limit deciding function for deciding whether each data element Xj is greater than $(\overline{X}-\sigma)$.

Reference numeral 31 designates a data upper limit deciding function for deciding whether each data element Xj is smaller than $(\overline{X}+\sigma/2)$.

If a data element Xj satisfies these two conditions i.e., Xj$\geq(\overline{X}-\sigma)$ and Xj$\leq(\overline{X}+\sigma/2)$, that data element Xj is added to the sum Z of the accepted data elements in a data element summing function 32. Also, the number J of the accepted data elements is increased by one by a function 33 which counts up the number of the accepted data elements.

Reference numeral 34 is a function for deciding whether the second processing of the number I of the data elements as selected in the first processing is completed. Reference numeral 37 is a function for incrementing data element number j to j+1 until the second data processing is completed.

Accordingly, the arrangement comprising the initializing function 29, data lower limit deciding function 30, data upper limit deciding function 31, data element summing function 32, the number of accepted date counting up function 33, completion of final data acceptance process deciding function 34 and data element number incrementing function 37 serves to accept, among the number I of data elements $Xj(J=1, 2 \ldots I)$, only those data elements that satisfy the requirement $\bar{x}-\sigma \leq xj \leq \bar{x}+\sigma/2$ to sum these data elements and to count up the number J thereof.

Reference numeral 35 designates a second average value calculating function which obtains a second average $\bar{x}=(Z/J)$ from the sum Z of data elements and the number J of accepted data elements. This second average value x is used as a measured value of the scattered light intensity and is output from a scattered light intensity measured value outputting function 36.

As noted, the lower limit for the acceptance of the number I of data elements Xj is $\bar{x}-\sigma$ while the upper limit is $X+\sigma/2$. This is based upon the fact that the effect of the unnecessary scattered light due to the dust, air bubbles, other particles present in the sample acts to add to the intensity of scattered light that is scattered by the substance to be measured. The above unbalanced setting of lower and upper limits relative to the average x effectively suppresses the adverse effect.

The above exemplified second screening (acceptance) range extends from $\bar{x}-\sigma$ to $(\bar{x}+\sigma/2)$. This is generalized to extend from $(\bar{x}-a_1\sigma)$ to $(\bar{x}+a_2\sigma)$ wherein $a_1$ is a constant greater than the constant $a_2$.

It is important that the center point of the second screening range be lower than the first average value.

Further, the coefficient of variation cv may be obtained from the average value $\bar{x}$ given by the first average value calculating function 24 and the standard deviation $\sigma$ given by the standard deviation calculating function 25 in accordance with the formula $cv=(\sigma/x)$. If the measured cv becomes greater than a constant value, alarm means may be activated to indicate that too much unnecessary scattered light exists in the sample.

Instead of using a constant value as a threshold level for coefficient of variation cv, it is possible and advantageous to employ a variable threshold level which is expressed as a function of average value x because the coefficient of the variation tends to increase as the light intensity decreases.

For example, it is proposed that the threshold level CVTH defining the critical point for activating the alarm may vary in accordance with a formula $$CVTH = \frac{K_2}{\sqrt{x}}$$

(where $K_2$ is constant). This is of great practical use.

From the forgoing description of the construction and operation of this invention, it is noted that this invention can provide a highly accurate and reliable measured result.

While the specific embodiment has been described and shown, it should be appreciated that various modifications thereof can be made without departing from the scope of the invention as defined by the following claims.

What is claimed is:

1. A laser nephelometric system for measuring the concentration of substances to be measured in a solution comprising:

(a) a laser unit for applying a beam of laser waves to the solution to obtain the light waves scattered therein, (b) means for receiving said scattered light waves to convert into corresponding electric signals in an analogue form, (c) means for converting said analogue signals to digital signals, (d) means for storing a predetermined number of said digital signals as a group of data elements, (e) means for searching a minimum data element out of said group as a first lower limit, (f) means for obtaining a first upper limit which is greater than and determined by said minimum data element, thus defining a first range, (g) means for selecting those data elements only that are within said first range, thus defining a first set of selected data elements, (h) means for averaging said first set of selected data elements to obtain a first average value, (i) means for obtaining second upper and lower limits from said first average value and a deviation parameter in said first set of selection data elements, thus defining a second range including said first average value, (j) means for selecting those data elements only that are within said second range, thus defining a second set of selected data elements, (k) means for averaging said second set of selected data elements to obtain a second average value which is used as a measured value of the intensity of scattered light due to the substances to be measured.

2. The system as claimed in claim 1 wherein said first upper limit is determined from said first lower limit (minimum data element) in such a manner that the ratio of the difference therebetween to the first lower limit decreases as the first lower limit increases so that it accords with the fact that the relative variation in the scattered light intensity decreases as the scattered light intensity increases.

3. The system as claimed in claim 2 wherein said first upper limit is expressed by $Xmin\ (1+k/\sqrt{Xmin})$ wherein Xmin is the value of said minimum data element and K is constant.

4. The system as claimed in claim 1 wherein the center point of said second range is lower than said first average value.

5. The system as claimed in any one of the preceding claims wherein said second range extends from $X-a_1\sigma$ to $X+a_2\sigma$ wherein X is said first average value and $\sigma$ is the standard deviation with respect to said first set of selected data elements and $a_1$ is a constant greater than the constant $a_2$.

* * * * *